US010257287B2

(12) United States Patent
Protas et al.

(10) Patent No.: US 10,257,287 B2
(45) Date of Patent: Apr. 9, 2019

(54) REAL-TIME DATA DISTRIBUTION SYSTEM FOR PATIENT MONITORING DEVICES, CARDIAC DEFIBRILLATORS AND ASSOCIATED INFORMATION DELIVERY SYSTEMS

(71) Applicant: Physio-Control, Inc., Redmond, WA (US)

(72) Inventors: Cheryl Protas, Pleasanton, CA (US); James Wootten, Kirkland, WA (US); Seshadri Kumar Padmanabha, Redmond, WA (US); Ken Peterson, Bellevue, WA (US); Randy Merry, Woodinville, WA (US); David Stewart, Carnation, WA (US)

(73) Assignee: Physio-Control, Inc., Redmond, WA (US)

( * ) Notice: Subject to any disclaimer, the term of this patent is extended or adjusted under 35 U.S.C. 154(b) by 344 days.

(21) Appl. No.: 14/470,880

(22) Filed: Aug. 27, 2014

(65) Prior Publication Data

US 2015/0067021 A1    Mar. 5, 2015

Related U.S. Application Data

(60) Provisional application No. 61/871,271, filed on Aug. 28, 2013.

(51) Int. Cl.
*H04L 29/08* (2006.01)
*G06F 19/00* (2018.01)
(Continued)

(52) U.S. Cl.
CPC .............. *H04L 67/16* (2013.01); *G06F 19/00* (2013.01); *G06F 19/3418* (2013.01);
(Continued)

(58) Field of Classification Search
None
See application file for complete search history.

(56) References Cited

U.S. PATENT DOCUMENTS 6,579,231 B1    6/2003  Phipps
6,697,103 B1*   2/2004  Fernandez ....... G08B 13/19608
                                                    348/143
(Continued)

FOREIGN PATENT DOCUMENTS

WO    WO 2008/098346 A1    8/2008

OTHER PUBLICATIONS

Lee et al.; "Biomedical Telemedicine"; Handout; CSCI-170; Jan. 11, 2005; 16 pages
(Continued)

*Primary Examiner* — Viet D Vu
*Assistant Examiner* — James A Edwards
(74) *Attorney, Agent, or Firm* — McDonnell Boehnen Hulbert & Berghoff LLP

(57) ABSTRACT

A data distribution system in comprises software application nodes that utilize a publish-subscribe communication mechanism for distribution of data in real-time or near real-time within a personal area network (PAN), local area network (LAN), or wide-area network (WAN) configuration. The distributed system communication software application nodes reside in medical devices, such as monitoring devices and cardiac defibrillators, and associated patient information delivery systems and patient data management systems comprising medical software installed on servers and end-user computing devices, including mobile devices.

20 Claims, 2 Drawing Sheets

(51) Int. Cl.
*G16H 40/63* (2018.01)
*G06F 15/173* (2006.01)
*A61B 5/00* (2006.01)
*H04L 12/46* (2006.01)
*H04W 4/80* (2018.01)

(52) U.S. Cl.
CPC ............ *G16H 40/63* (2018.01); *H04L 67/10* (2013.01); *A61B 5/0022* (2013.01); *G06F 15/173* (2013.01); *H04L 12/4604* (2013.01); *H04L 29/08* (2013.01); *H04W 4/80* (2018.02)

(56) References Cited

U.S. PATENT DOCUMENTS

| | | | | |
|---|---|---|---|---|
| 6,790,044 | B1* | 9/2004 | Hagebarth | G09B 5/065 434/322 |
| 7,349,947 | B1* | 3/2008 | Slage | G06F 19/363 705/2 |
| 7,614,001 | B2* | 11/2009 | Abbott | G06F 1/163 706/45 |
| 7,733,244 | B2 | 6/2010 | Tran | |
| 8,185,623 | B2* | 5/2012 | Lewis | G06F 19/322 340/539.12 |
| 8,591,455 | B2 | 11/2013 | Mensinger et al. | |
| 8,684,922 | B2 | 4/2014 | Tran | |
| 8,750,971 | B2 | 6/2014 | Tran | |
| 8,755,821 | B2* | 6/2014 | Brisebois | G01S 5/00 455/456.1 |
| 8,764,651 | B2* | 7/2014 | Tran | A61B 5/0022 600/300 |
| 9,079,306 | B2* | 7/2015 | Ng-Thow-Hing | |
| 2002/0019584 | A1 | 2/2002 | Schulze et al. | |
| 2002/0129106 | A1* | 9/2002 | Gutfreund | G06Q 10/10 709/205 |
| 2004/0054918 | A1* | 3/2004 | Duri | G06Q 20/382 726/1 |
| 2008/0101160 | A1 | 5/2008 | Besson | |
| 2009/0054735 | A1* | 2/2009 | Higgins | A61B 5/0006 600/300 |
| 2009/0099480 | A1* | 4/2009 | Salgo | A61B 5/103 600/595 |
| 2009/0105879 | A1* | 4/2009 | Ng-Thow-Hing | B25J 9/1656 700/245 |
| 2009/0177477 | A1* | 7/2009 | Nenov | A61B 5/0002 704/275 |
| 2010/0205205 | A1* | 8/2010 | Hamel | G06F 17/30286 707/769 |
| 2010/0315225 | A1* | 12/2010 | Teague | A61B 5/0024 340/539.12 |
| 2011/0125921 | A1* | 5/2011 | Karenos | H04L 45/00 709/240 |
| 2011/0161103 | A1* | 6/2011 | Dye | G06F 19/3487 705/2 |
| 2012/0242501 | A1* | 9/2012 | Tran | A61B 5/0024 340/870.02 |
| 2013/0024213 | A1* | 1/2013 | Poon | A61B 5/0002 705/3 |
| 2013/0099918 | A1 | 4/2013 | Dunst et al. | |
| 2014/0028464 | A1* | 1/2014 | Garibaldi | G06F 19/3443 340/870.02 |

OTHER PUBLICATIONS

Powers; Status of a Commercial Physiological Status Monitoring (PSM) System; QinetiQ North America; 2009; 14 pages.
Arulogun; "IPv6 Based Wireless Sensor Networks Electronic Health Monitoring System"; Proceedings of the Fourth Int'l Conf. on Mobile e-Services; vol. 4; Oct. 2012; p. 11-17.
"BioHarness 3 Team Compression Shirts"; www.zephyranywherestore.com/BioHarness-3-Team-Compression-Shirts/dp/B009ZT; Zephyr Technology Corp.; 2012; accessed Sep. 9, 2014, 2 pages.
"5 wearable technolgies for EMS"; www.ems1.com/technology/articles/1861982-5-wearable-technologies-for-EMS; 2014; access Sep. 9, 2014; 3 pages.
"High Fidelity Alarm Analytics"; www.visimobile.com/visi-product-info/high-fidelity-alarm-analytics/; access Sep. 9, 2014; 2 pages.
Koemer; "Your Cellphone is a Homing Device"; www.legalaffairs.org/issues/July-August-2003/feature_koerner_iulaug03.msp); Jul./Aug 2003; accessed Sep. 10, 2014; 6 pages.
Patel et al.; "A Review of Wearable Sensors and Systems with Applications in Rehabilitation"; Journal of Neuroengineering and Rehab; 2012; 9:21; p. 1-17.

\* cited by examiner

REAL-TIME DATA DISTRIBUTION SYSTEM FOR PATIENT MONITORING DEVICES, CARDIAC DEFIBRILLATORS AND ASSOCIATED INFORMATION DELIVERY SYSTEMS

CROSS-REFERENCE TO RELATED APPLICATIONS

This application claims benefit under 35 U.S.C. § 119(e) of Provisional U.S. patent application No. 61/871,271, filed Aug. 28, 2013, the contents of which is incorporated herein by reference in its entirety.

TECHNICAL FIELD

The present invention relates generally to medical devices including defibrillators, and more particularly to a data distribution system configured to distribute patient medical data in real-time or near real-time.

SUMMARY

A data distribution system in accordance with an illustrative embodiment comprises a personal area network (PAN) comprising a first PAN node and a second PAN node, and a PAN data blackboard, wherein the first PAN node comprises a first medical device configured for monitoring a first patient. In addition, the inventive system may include a wide area network (WAN) comprising a WAN data blackboard coupled to the PAN data blackboard, and a WAN data management node. The PAN data blackboard is configured to provide a data storage space shared among the first and second PAN nodes. In the illustrative embodiment, data blackboards are used in PAN, LAN, and WAN communications, and a separate blackboard is used for each type of communication.

In the illustrative embodiment, the first PAN node is configured as publisher node, whereby the first PAN node writes data to the PAN data blackboard, and the second PAN node is configured as a subscriber node, whereby the second PAN node reads data from the PAN data blackboard. The data distribution system of the illustrative embodiment also includes a local area network (LAN) comprising a first LAN node, a second LAN node, a LAN data blackboard, and a LAN data management node. As discussed below, a WAN data blackboard may also be used for WAN communications.

Other features of the illustrative embodiment are described below.

DETAILED DESCRIPTION OF ILLUSTRATIVE EMBODIMENTS

Data Distribution System and Method

An illustrative embodiment of a data distribution system in accordance with the present invention comprises software application nodes that utilize a publish-subscribe communication mechanism for distribution of data in real-time or near real-time within a personal area network (PAN), local area network (LAN), or wide-area network (WAN) configuration. The distributed system communication software application nodes reside in medical devices, such as monitoring devices and cardiac defibrillators, and associated patient information delivery systems and patient data management systems comprising medical software installed on servers and end-user computing devices, including mobile devices.

Figure 1:
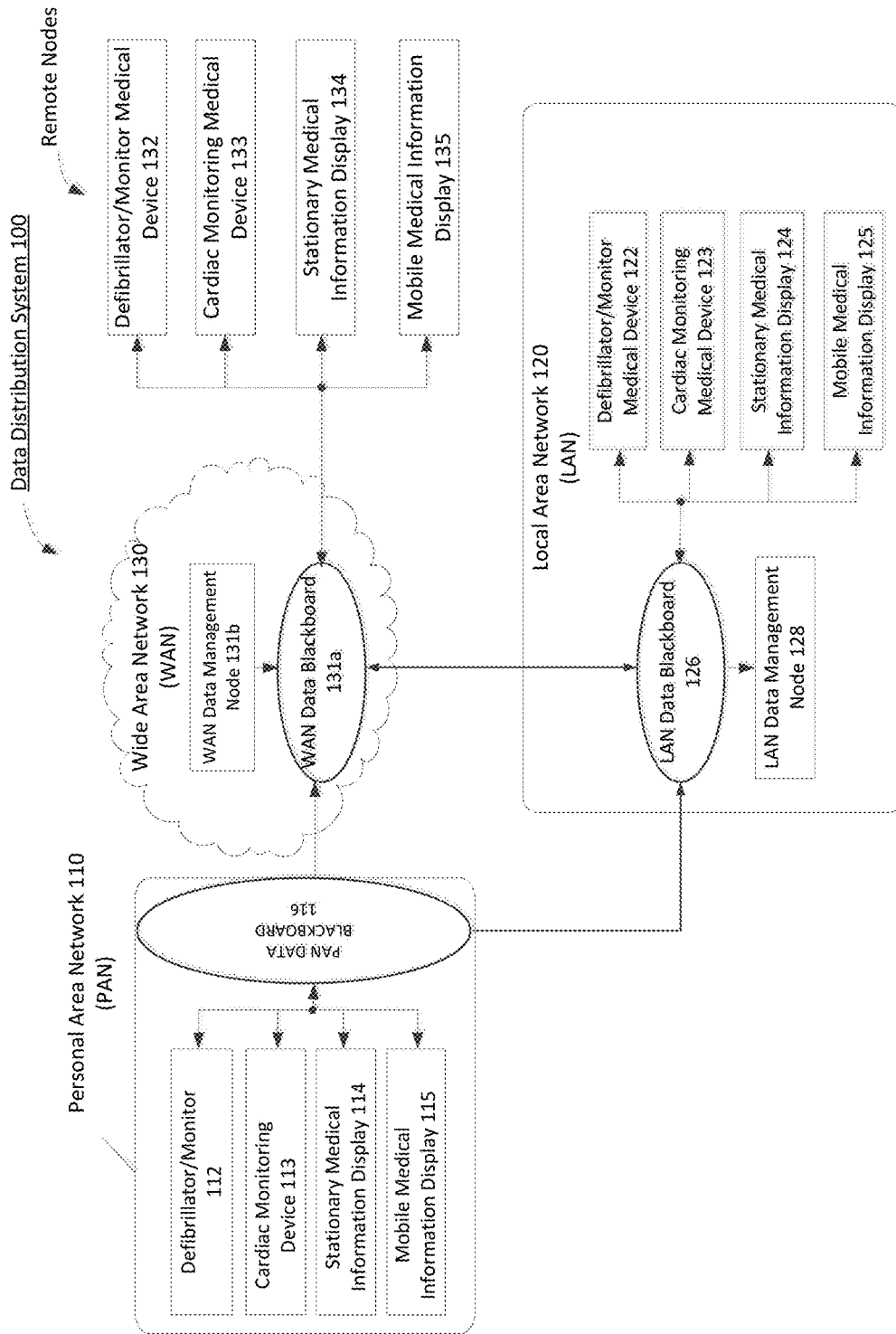
FIG. 1 is a block diagram of an illustrative embodiment of a data distribution system in accordance with the present invention.

Referring to FIG. 1, in the illustrative embodiment, the data distribution system 100 may include or employ a personal area network (PAN) 110, a local area network (LAN) 120, and/or a wide area network (WAN) 130. The PAN 110 includes various nodes, including a defibrillator/monitor 112, a cardiac monitoring device 113, a stationary medical information display 114, and a mobile medical information display 115. It will be understood by those skilled in the art that these are just exemplary medical sensing or display devices, and that a given system may include only a subset of these or all of these plus additional nodes. The nodes are operatively connected to a PAN data blackboard 116. Each of the various nodes can be configured as a "publisher" or "subscriber" of data (or both), and the PAN data blackboard and the other blackboards (i.e., 126 and 131a) provide a data space that can be shared by the connected publisher and subscriber nodes. As used herein, the term "blackboard" refers to a shared memory structure.

Similarly, the LAN 120 includes various nodes including a defibrillator/monitor medical device 122, a cardiac monitoring device 123, a stationary medical information display 124, and a mobile medical information display 125. Here again, it will be understood by those skilled in the art that these are just exemplary medical sensing or display devices, and that a given system may include only a subset of these or all of these plus additional nodes. The nodes are operatively connected to a LAN data blackboard 126, and the LAN data blackboard 126 is connected to a LAN data management node 128. The LAN data management node 128 (as well as the WAN data management node 133) is configured to mediate the communication channels, ensuring subscribers have access to published data they are entitled to access, and do not have access to published data they are not entitled to access. The data management nodes may also perform certain processor intensive activities (in other words, data analytics) and long term data storage tasks.

Finally, referring to FIG. 1, the WAN 130 includes the WAN data blackboard 131a and the WAN data management node 131b, and is operatively connected to various nodes, e.g., a defibrillator/monitor medical device 132, a cardiac monitoring device 133, a stationary medical information display 134, and a mobile medical information display 135. It should be noted that the number of subscribers/publishers, including medical device nodes, is limited by the available resource on the particular network configuration. For example, a single PAN may support approximately 5-10 devices depending on wireless capability, bandwidth, memory constraints at each node, processing constraints at each node, etc. On the other hand, a single LAN may support hundreds of devices (concurrently), and a WAN may support thousands of devices (concurrently).

The overall data distribution system 100 can:
- Be localized to devices connected in an ad-hoc personal area network (PAN).
- Be geographically dispersed via a wide area network (WAN), i.e., by way of wired or wireless connections of nodes over the Internet.

Be a local area network (LAN) or virtualized local area network (VLAN) of wired or wirelessly connected nodes.

Comprise various computing hardware and operating systems.

Enable all nodes to publish information to other nodes and subscribe to information from other nodes.

Ensure multiple subscriber nodes can receive medical event information that is published just once by another node.

Medical Data Monitoring and Distribution Method

Figure 2:
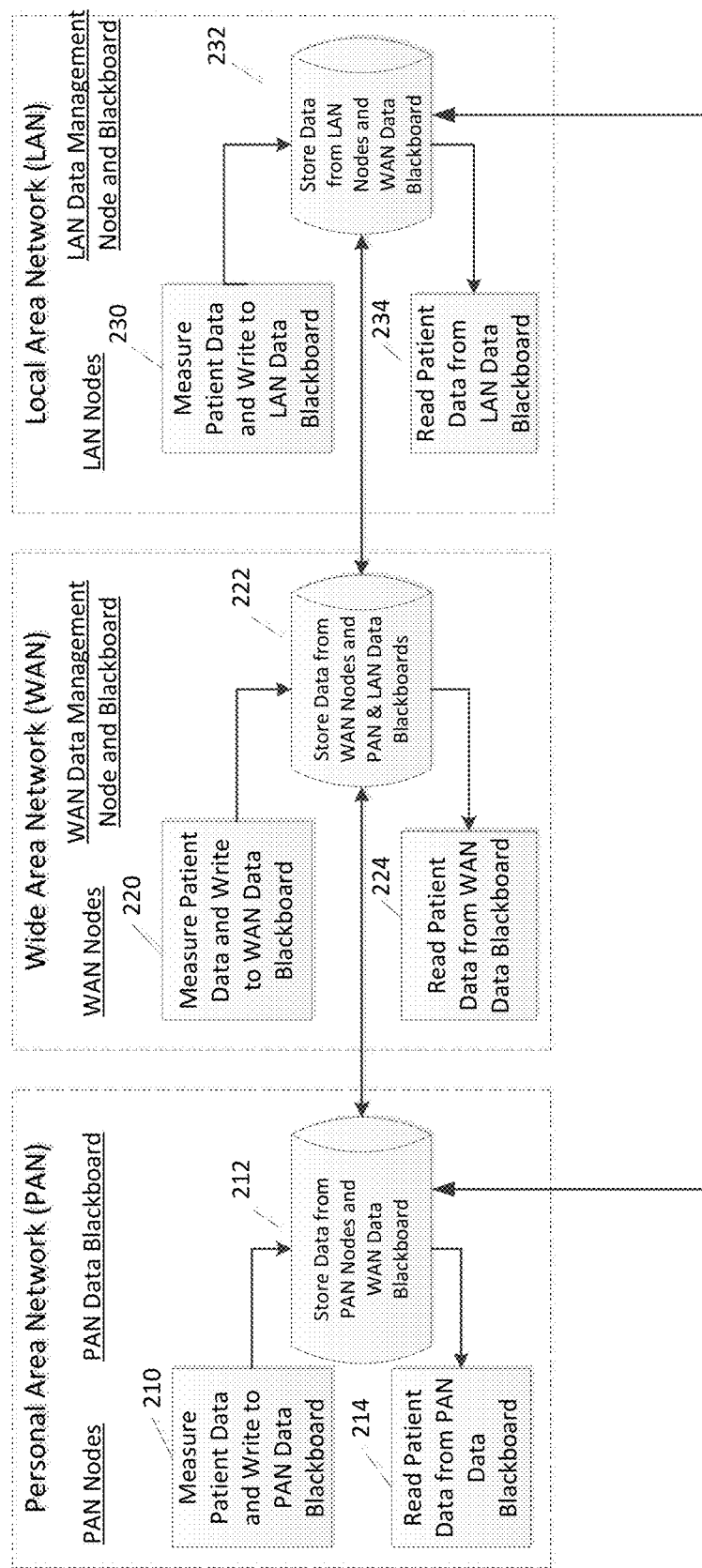
FIG. 2 is a flowchart of a medical data monitoring and distribution method in accordance with the present invention.

FIG. 2 depicts an illustrative embodiment of a medical data monitoring and distribution method in accordance with the present invention. As discussed above, the inventive system operates according to a method in which a first node of a personal area network (PAN) is used to monitor a first patient and write medical data to a PAN data blackboard. A second PAN node, which may be contained within in a second medical device, reads data from the PAN data blackboard. Moreover, as discussed, the PAN data blackboard may be coupled to a WAN data blackboard, which may in turn be coupled to a remote LAN data blackboard, and both the WAN and LAN data blackboards may be coupled to respective medical devices and nodes.

As shown in FIG. 2, in a PAN, a first PAN node measures patient data and writes this data to the PAN data blackboard (step 210). The PAN data blackboard stores the data and may also store selected data from the WAN data blackboard (step 212); and a second LAN node reads selected data from the PAN data blackboard (step 214).

Similarly, in a WAN, a first WAN node measures patient data and writes this data to the WAN data blackboard (step 220), and the WAN data blackboard stores the data and may also store selected data from the PAN and LAN data blackboards (step 222). A second WAN node may be deployed to read selected data from the WAN data blackboard (step 224).

Finally, in the LAN (far right box of FIG. 2), a first LAN node measures patient data and writes this data to the LAN data blackboard (step 230). The LAN data blackboard stores the data and may also store selected data from the WAN data blackboard (step 232); and a second LAN node reads selected data from the LAN data blackboard (step 234).

Further Details of Illustrative Uses

The inventive data distribution system and method may be used to:

Distribute medical event information between local and remote nodes in the data distribution system. Such medical event information can include data, audio and video streams, and consumable electronic object formats.

Distribute information for shared viewing of information that is continuously updated (i.e., in "real-time" or by "live streaming") on one or more subscribing nodes when changed on the publisher node. For example, an ECG lead sensor reading may be distributed every 0.25 ms, or updated on a discrete interval, or may be considered a "batch" mode operation where information is bundled periodically on a publisher node and broadcast to subscriber nodes. For example, a sync timer may be used, or an intermittent event; for example, a lead placement indicator may be used.

Distribute software and configuration updates within the data distribution system.

Distribute commands between local and remote nodes in the data distribution system. A distributed command is an instruction by one node to one or more other nodes to perform an action. An example is a command to start a timer, silence an alarm, etc.

Conduct remote diagnostics of equipment.

Distribute algorithms for processing ("analytics") across nodes of the data distribution system.

Data Blackboard (see elements 116, 126, and 131*a* in FIG. 1)—a data space shared among connected publisher and subscriber nodes to enable publication (write) and subscription (read).

Node (see elements 112-115, 122-125, and 132-135 of FIG. 1)—each node is a publisher/subscriber of a Data Blackboard. Node Types may include Information Management System, Defibrillator/Monitor, Monitoring Device, Stationary Medical Information Display, Mobile Medical Information Display.

PAN Data Distribution System: nodes dynamically form a wireless personal area network based on close proximity (e.g., patient home, military battle field, movie theater) sharing a Data Blackboard for point-to-point publish-subscribe communication within the PAN. Many PAN instances may exist concurrently.

LAN Data Distribution System: wired and wireless nodes participate in a local area network. Wireless nodes join the network via one or more network access points. LAN nodes participate in publish-subscribe communication using LAN network infrastructure. LANs are created for organizational entities such as a patient care facility (e.g., Hospital, Emergency Room), or patient care organization (e.g., Hospital Network)

WAN Data Distribution System: Servers residing in data centers enable publishers and subscribers to span a broader geographic spectrum than a PAN or LAN. The WAN servers bridge the communication between PAN and LAN nodes, as well as publish-subscribe nodes connected directly.

Each Data Blackboard selectively synchronizes data with other Data Blackboards, thereby enabling communication with nodes connected to another bus. The Data Management Nodes mediate the communication channels, ensuring subscribers have access to published data they are entitled to access, and do not have access to published data they are not entitle to access. The Data Management Nodes may also offload processor intensive activities and long term data storage requirements from other Data Distribution System nodes.

Further Illustrative Details of How it Works

Node Capability:

Each node in the distributed system has the capability to both publish (provide data) and subscribe (consume data). The communication nodes participate in the distributed system as either publishers, or subscribers, or both.

A subscriber may perform content filtering on published streams. In other words, a subscriber can be selective regarding what it receives from a publisher. In other words, a publisher may publish more than the subscriber receives.

Data Types:

Each node publishes and\or subscribes to a data channel for exchange of discrete data, audio and video streams, and binary objects.

Data Sources:

The data source for publication may be bio-sensors, medical information systems, externally connected medical device accessories, user entered information, and/or the results from algorithms/processor intensive activities/data summarization of a node.

Communication Channel Types:
   Distributed system nodes may communicate in the data distribution system via wired network connection or wireless network connection. Wireless network connections include Wi-Fi™, Wi-Fi Direct™ and Bluetooth® Standard, Bluetooth® PAN, and Cellular.

Communication Channel Middleware:
   The data distribution system may include messaging middleware that enables the publishers and subscribers to function autonomously (i.e., "decoupled").

Communication Protocol and Data Format Standards
   The Data Distribution System may implement a standard messaging protocol for publish-subscribe communications such as Message Queuing for Telemetry Transport (MQTT) or Advanced Message Queuing Protocol.
   The Data Distribution System may alternatively comprise shared data spaces, which also decouples publishers and subscribers. A standard protocol for distributed data communication using shared data spaces is the Object Management Group Data-Distribution Service for Real-Time Systems (DDS).
   Other standard protocols for communication are UDP and TCP/IP
   Data payload may employ data format and\or semantics as defined by the following standards: IEEE 11073, HL7, IHE Domains such as Infrastructure, PCD, and the IHE CDA\CCD, and NEMSIS XML.

Communication Attributes:
   Published data is persistent; a "late" subscriber may obtain published data for a defined interval following its publication.
   Publication is reliable; a publisher will postpone publication until a lost connection is restored or an unavailable connection becomes available.
   The publication is auto-scaled (also "auto-adjusted") based on available bandwidth, thereby reducing or increasing the amount or frequency of data, or selectively eliminating lower-priority data to give bandwidth for higher priority data.
   The publication/subscription capability on each node minimizes bandwidth requirement and battery consumption, thereby allowing interconnected mobile battery powered nodes.
   Publication may be multi-cast (many publishers, many subscribers) or unicast (one publisher, one subscriber).

Communication Isolation
   The Data Distribution System enforces constraints necessarily to ensure data privacy and to enable nodes to operate within resource limitations (memory, storage, battery, etc.); publishers are necessarily constrained by where to publish, when to publish, and what to publish. Subscribers are constrained by which publications they have access to, when they receive the publication, and how much they can receive due to limited subscriber resources (memory, storage, battery, etc.).

Communication Sustainability Across Networks
   Distributed system nodes may participate in publish-subscribe communications over several network interfaces concurrently or serially.
   The data distribution system enables a bridge for communications across network interfaces, allowing publishers and subscribers to reside on separate networks.
   Distributed system nodes including publishers and subscribers may switch network connections, allowing a subscriber to continue to receive data from a publisher after the switchover.
   Distributed system nodes may implement a priority scheme to expedite a connection switch based on connection speed, connection strength, or service discovery\accessibility.

CONCLUSION

One skilled in the art will appreciate that the present teachings can be practiced with embodiments other than those disclosed above. The disclosed embodiments are presented for purposes of illustration and not limitation. The scope of protection of the following claims is limited only by the claims themselves and not by the above description.

We claim:

1. A data distribution system, comprising:
   a first personal area network (PAN) node, a second PAN node, and a PAN data blackboard coupled to the first and second PAN nodes via a PAN, wherein the PAN data blackboard comprises a first shared memory structure having a first data storage space, wherein the first PAN node comprises a first medical device configured for monitoring a first patient and writing patient medical data concerning the first patient to the first data storage space in real-time, and wherein the second PAN node comprises a second medical device configured for reading the patient medical data from the first data storage space and displaying the patient medical data in real-time;
   a first local area network (LAN) node and a LAN data blackboard coupled to the first LAN node, wherein the LAN data blackboard is coupled to the PAN data blackboard via a LAN, wherein the LAN data blackboard comprises a second shared memory structure having a second data storage space, wherein the LAN data blackboard comprises a LAN data management node configured to determine that the first LAN node is entitled to access the patient medical data and to selectively synchronize data with the PAN data blackboard such that the patient medical data is stored in the second data storage space for retrieval in real-time by the first LAN node, and wherein the first LAN node comprises a third medical device configured for reading the patient medical data from the second data storage space and displaying the patient medical data in real-time; and
   wherein the system is configured in accordance with a publish-subscribe messaging model in which nodes that are senders of messages (publishers) do not program the messages to be sent directly to specific receivers (subscribers) but instead categorize published messages into classes without knowledge of which subscribers, if any, there may be, and send the messages to an associated blackboard, and
   wherein each of the nodes is configured as a publisher or subscriber of data, or both a publisher and subscriber of data.

2. The data distribution system recited in claim 1, wherein the first PAN node is configured as publisher node, and wherein the second PAN node is configured as a subscriber node.

3. The data distribution system recited in claim 2, further comprising
   a first wide area network (WAN) node and a WAN data blackboard coupled to the first WAN node, wherein the WAN data blackboard is coupled to the PAN data blackboard via a WAN, wherein the WAN data blackboard comprises a third shared memory structure having a third data storage space, wherein the WAN data blackboard comprises a WAN data management node configured to determine that the first WAN node is entitled to access the patient medical data and to selectively synchronize data with the PAN data blackboard such that the patient medical data is stored in the third data storage space, and wherein the first WAN node comprises a fourth medical device configured for reading the patient medical data from the third data storage space and displaying the patient medical data in real-time.

4. The data distribution system recited in claim 3, wherein the first data storage space is shared among the first PAN node and the second PAN node, wherein the second data storage space is shared among the first LAN node and a second LAN node coupled to the LAN data blackboard, and wherein the third data storage space is shared among the first WAN node and a second WAN node coupled to the WAN data blackboard.

5. The data distribution system recited in claim 4, wherein the first WAN node is configured as a subscriber node, and wherein the second WAN node is configured as a publisher node.

6. The data distribution system recited in claim 1, wherein the first PAN node comprises a first software application node residing in the first medical device, and the second PAN node comprises a second software application node residing in the second medical device.

7. The data distribution system recited in claim 6, wherein the first LAN node comprises a third software application node residing in the third medical device, and the second LAN node comprises a fourth software application node residing in a fourth medical device.

8. The data distribution system recited in claim 7, wherein the first WAN node comprises a fifth software application node residing in a fifth medical device, and wherein the second WAN node comprises a sixth software application node residing in a sixth medical device.

9. The data distribution system recited in claim 8, wherein at least one of the first, second, third, fourth, fifth, or sixth medical devices is a cardiac defibrillator or cardiac monitoring device.

10. The data distribution system recited in claim 1, wherein the patient medical data comprises an electrocardiogram sensor reading.

11. The data distribution system recited in claim 1, wherein the patient medical data comprises an audio stream or a video stream.

12. A medical data monitoring and distribution method, comprising:
  in a personal area network (PAN) comprising a first PAN node within a first medical device, a second PAN node within a second medical device, and a PAN data blackboard:
    employing the first PAN node and first medical device to monitor a first patient and to write medical data concerning the first patient to a first data storage space of the PAN data blackboard in real-time, and
    employing the second PAN node and second medical device to read the patient medical data from the first data storage space and display the patient medical data in real-time; and
  in a local area network (LAN) comprising a first LAN node and a LAN data blackboard coupled to the PAN data blackboard via the LAN:
    determining, by a LAN data management node of the LAN data blackboard that the first LAN node is entitled to access the patient medical data,
    selectively synchronizing, by the LAN data management node, data with the PAN data blackboard such that the patient medical data is stored in a second data storage of the LAN data blackboard for retrieval in real-time by the first LAN node,
    reading, by the first LAN node, the patient medical data from the second data storage space, and
    displaying, by the first LAN node, the patient medical data in real-time,
  wherein the PAN and the LAN are configured in accordance with a publish-subscribe messaging model in which nodes that are senders of messages (publishers) do not program the messages to be sent directly to specific receivers (subscribers) but instead categorize published messages into classes without knowledge of which subscribers, if any, there may be, and send the messages to an associated blackboard, and
  wherein each of said nodes is configured as a publisher or subscriber of data, or both a publisher and subscriber of data.

13. The medical data monitoring and distribution method recited in claim 12, further comprising:
  coupling a wide area network (WAN) data blackboard to the LAN; and
  selectively synchronizing, using a WAN data management node of the WAN data blackboard, data with the PAN data blackboard such that the patient medical data is stored in a third data storage space of the WAN data blackboard.

14. The medical data monitoring and distribution method recited in claim 13, further comprising coupling a first WAN node and a second WAN node to the WAN data blackboard.

15. The medical data monitoring and distribution method recited in claim 14, further comprising:
  writing data to the WAN data blackboard using the first WAN node; and
  reading data from the WAN data blackboard using the second WAN node.

16. The medical data monitoring and distribution method recited in claim 15, wherein the first PAN node comprises a first software application node residing in the first medical device, and the second PAN node comprises a second software application node residing in the second medical device.

17. The medical data monitoring and distribution method recited in claim 16, wherein the first LAN node comprises a third software application node residing in a third medical device.

18. The medical data monitoring and distribution method recited in claim 17, wherein at least one of the first, second, or third medical devices is a cardiac defibrillator or cardiac monitoring device.

19. The medical data monitoring and distribution method recited in claim 12, wherein the patient medical data comprises an electrocardiogram sensor reading.

20. The medical data monitoring and distribution method recited in claim 12, wherein the patient medical data comprises an audio stream or a video stream.

* * * * *